United States Patent [19]

Russ, deceased et al.

[11] Patent Number: 5,200,064
[45] Date of Patent: Apr. 6, 1993

[54] FUEL CONTAMINATION DETECTOR

[75] Inventors: Daniel G. Russ, deceased, late of Fort Wayne, by Ruth S. Russ, executrix; Vilmer L. Nichols, Fort Wayne; Steven E. Modezjewski, Fort Wayne; Michael R. Miller, Churubusco, all of Ind.

[73] Assignee: Telectro-Mek, Inc., Fort Wayne, Ind.

[21] Appl. No.: 659,822

[22] Filed: Feb. 22, 1991

[51] Int. Cl.$^5$ ............... G01N 33/28; G01N 1/34; G01N 21/88; G01N 21/01

[52] U.S. Cl. ............... 210/94; 73/61.71; 210/236; 356/38; 356/51; 356/70; 356/72; 356/244; 356/440; 356/442

[58] Field of Search ............ 73/61 R, 61.1 R, 863.23; 210/85, 96.1, 236, 323.1, 745, 94; 356/36, 51, 70, 72, 73, 244, 435, 440, 441, 442; 422/101; 436/40, 46, 60; 55/270

[56] References Cited

U.S. PATENT DOCUMENTS

| | | | |
|---|---|---|---|
| 617,343 | 1/1899 | Legg | 210/167 |
| 758,150 | 4/1904 | Schilling | 210/459 |
| 1,172,728 | 2/1916 | Perkins | 210/346 |
| 1,834,905 | 12/1931 | Sheldon | 356/244 |
| 2,144,444 | 1/1939 | Victor | 210/513 |
| 3,063,289 | 11/1962 | Moul | 73/61 R |
| 3,141,548 | 7/1964 | Newby | 356/244 |
| 3,500,046 | 3/1970 | Caldwell | 73/61.1 R |
| 3,510,194 | 5/1970 | Connelly | 356/244 |
| 3,790,279 | 2/1974 | Skala | 356/70 |
| 3,892,485 | 7/1975 | Merritt et al. | 356/70 |
| 4,044,604 | 8/1977 | Russ | 73/61 R |
| 4,045,139 | 8/1977 | Russ | 356/36 |
| 4,090,791 | 5/1978 | Siddiqi et al. | 356/244 |
| 4,193,694 | 3/1980 | Smith | 356/407 |
| 4,944,876 | 7/1990 | Miller | 210/321.75 |

OTHER PUBLICATIONS

IBM Technical Disclosure Bulletin, vol. 22 No. 3 "Holding Fixture for Thickness Measuring Apparatus", Wirtz and Yakubowski, Aug. 1979.

Millipore Bulletin, Application Guide AG-1, "Analysis and Control of Contamination in Aviation Fuels"; Jan. 22, 1968, Millipore Filter Corporation.

Primary Examiner—Robert A. Dawson
Assistant Examiner—Joseph Drodge
Attorney, Agent, or Firm—George Pappas

[57] ABSTRACT

A fuel contamination detection system for use in testing the contamination level of a fuel sample, wherein the system is selectively operable in a first mode as a particulate detector and in a second mode as a free water detector. A filter support slide includes two apertures and is adapted to support different sizes of filter elements over the apertures. In the particulate detector mode, the slide carries a pair of filter elements through which a fuel sample has been passed, wherein one filter element bears particulates from the sample. A particulate detection circuit includes an incandescent light and a photocell, between which the slide is moved to introduce one filter element and then the other, whereby a differential reading of their respective opacities is obtained and displayed. In the free water detector mode, only one aperture of the slide is used to carry a chemically treated water filter pad. A free water detector circuit includes an ultraviolet light and a photoresistor, adjacent which the slide is moved to expose the water filter pad to the ultraviolet such that the photoresistor responds to light fluorescing from the water filter pad, whereby a reading of the fluorescent light intensity is obtained and displayed. Optical switches cooperate with positioned holes in the filter support slide to provide slide position sensing that is used by the circuits for test sequencing and that provides visual prompts to a system operator.

18 Claims, 5 Drawing Sheets

FUEL CONTAMINATION DETECTOR

BACKGROUND OF THE INVENTION

The present invention relates generally to contamination detection systems for determining contamination levels in fluid samples and, more particularly, to such a system used in the testing of fuel samples to determine the particulate and free water levels in the fuel supply from which the sample is taken, thereby ensuring the delivery and use of clean, dry fuel.

A variety of particulate detection systems are currently used in laboratories and in field operations to determine contaminant levels in various fluid testing applications. For example, an important application for a contamination detection system is the testing of aircraft fuel supplies for unacceptable levels of particulate and free water contamination. Typically, two fuel samples are tested by a particulate detector and a free water detector, respectively, in accordance with a variety of testing methods.

Particulate detectors currently in use are based upon one of several conventional techniques utilizing a membrane filter on which particulates are deposited. The membrane filter is analyzed to determine the amount of particulates on the filter, thereby indicating the concentration of particulates in the fluid sample. The most common methods currently used to analyze the membrane filter are Gravimetric Assessment, Colormetric Assessment, or Visual Assessment.

The Gravimetric Assessment method of analyzing the membrane filter involves actual weighing of the particulate products retained on the membrane filter after the fluid has been passed therethrough. The Colormetric Assessment method involves evaluating the particulate laden membrane filter on the basis of coloration, hue, chroma, and intensity. The Visual Assessment method relies upon a skilled operator to correctly identify the quality and quantity of particulates deposited on the membrane filter.

As previously noted, particulate detection systems are used in the field testing of aircraft fuel supplies. One such fuel testing system is disclosed in U.S. Pat. No. 4,044,604, assigned to the assignee of the present invention, which utilizes the principle of differential light transmission through membrane filters to measure particulate contamination levels More specifically, a fuel sample is passed through a pair of membrane filters, wherein the first filter traps particulates and acquires fuel coloration while the second filter acquires only fuel coloration. Individual opacity readings are taken of the respective filters as they are successively placed in a single filter holder, and then a differential reading is manually calculated, whereby the differential reading represents a measure of particulate level independent of fuel coloration.

In each of the aforementioned methods of analyzing a membrane filter to determine the particulate count, the accuracy of the measurement is affected by excessive handling of the sample filter, resulting in filter contamination and measurement errors. Also, the prior art sample filter handling methods are cumbersome and necessitate long cycle times for conducting contamination tests.

The present invention is directed to overcoming the aforementioned problems associated with prior art contamination detection systems, wherein it is desired to provide an improved membrane filter handling apparatus that improves the accuracy of contamination test results, and minimizes the cycle time required to perform the tests. It is further desired to provide a fuel contamination detection system that combines a particulate detector and free water detector in an inexpensive, compact package.

SUMMARY OF THE INVENTION

The present invention overcomes the problems and disadvantages of the above-described prior art fuel contamination detection systems by providing an improved particulate detector, wherein a filter support slide accommodates two filter elements from which a differential opacity measurement is determined in order to provide an indication of the particulate level in a fluid sample, whereby handling of the filter elements by an operator is eliminated between respective opacity measurements, thereby minimizing possible filter contamination and errors in particulate level indications.

Generally, the present invention provides a particulate detector including a light source and a photosensor responsive to light intensity. A filter support slide includes a pair of apertures over which a reference filter element and a particulate bearing filter element are supported. The slide is selectively movable such that the filter elements may be alternatingly introduced intermediate the light source and the photosensor, whereby respective measurements of the opacities of the reference filter element and the particulate bearing filter element may be made. A differential opacity reading is computed and displayed, thereby providing an indication of particulate levels in the fluid sample.

More specifically, the present invention provides, in one form thereof, a filter support slide for use in a particulate detector having a light source, a photosensor, and circuitry for measuring the opacity of filter elements selectively introduced intermediate the light source and the photosensor by movement the slide. The position of the slide is sensed in order to instruct the circuitry and an operator as to which operation is to be performed at that position, i.e., the input of a manual adjustment or the observation of a test result. In one aspect of the invention, the operator may be prompted to manually adjust the circuitry to provide a reference reading when the slide is in a first position, and then be prompted to observe a differential reading of the opacities when the slide is in a second position.

In a further aspect of the present invention, in one form thereof, a fuel contamination detection system is provided including the aforementioned particulate detector and a free water detector The aforementioned slide associated with the particulate detector is also adapted to support a free water pad that, upon movement of the slide to a predetermined position, is exposed to an ultraviolet light source. A photoresistor and associated circuitry measure the intensity of light fluorescing from the water filter pad. An indication of the light intensity measurement is provided, representing the level of free water in a fuel sample. Specifically, the operator first manually adjusts the circuitry to provide a reference reading of the water filter pad before the fuel sample is passed therethrough, and then the wetted water filter pad is tested to determine the free water level.

An advantage of the fluid contamination detection system of the present invention is that both of the filter elements used for determining particulate levels are handled simultaneously by a single filter support slide, thereby facilitating expeditious testing and minimizing the possibility of filter contamination and measurement error.

Another advantage of the fluid contamination detection system of the present invention is that sequencing of particulate level testing is automatically effected by movement of the filter support slide.

A further advantage of the fluid contamination detection system of the present invention is that an operator is prompted to provide manual inputs at appropriate points during the testing sequence.

Yet another advantage of the fluid contamination detection system of the present invention is that the filter support slide is capable of accommodating filter elements of different sizes, depending on commercial or laboratory standards.

A still further advantage of the fluid contamination detection system of the present invention is that an operator is provided with a direct indication of the particulate level in the fluid sample without further manual calculations.

Another advantage of the fluid contamination detection system of the present invention is the provision of a combined particulate detector and free water detector, wherein a single filter handling slide is used for either testing mode.

The invention, in one form thereof, provides a particulate detector for a fluid contamination detection system, wherein a fluid sample containing particulates is passed successively through a first filter element that both traps the particulates and acquires the coloration of the fluid sample and a second filter element that only acquires the coloration of the fluid sample. Specifically, the particulate detector includes a light source, a photosensor that provides an indication of the intensity of the light source, and a filter support slide for handling the aforementioned filter elements. The filter support slide includes a first aperture and a second aperture, and is movable between a first position whereat the first aperture is intermediate the light source and the photosensor, and a second position whereat the second aperture is intermediate the light source and the photosensor. The slide is adapted to support the first filter element over the first aperture and the second filter element over the second aperture, thereby causing the first and second filter elements to be intermediate the light source and the photosensor when the slide is in the first and second positions, respectively. The opacities of the first and second filter elements are measured by circuitry responsive to the photosensor when the slide is in the first and second positions, respectively. The particulate detector provides an indication of particulate levels in the fluid sample based upon the measured opacities of the first and second filter elements. It can be seen that detection of particulate levels in the fluid sample is performed without further handling of the first and second filter elements once they are placed in supporting relationship on the filter support slide, thereby minimizing filter contamination and resulting measurement error.

DESCRIPTION OF THE PREFERRED EMBODIMENT

Figure 1:
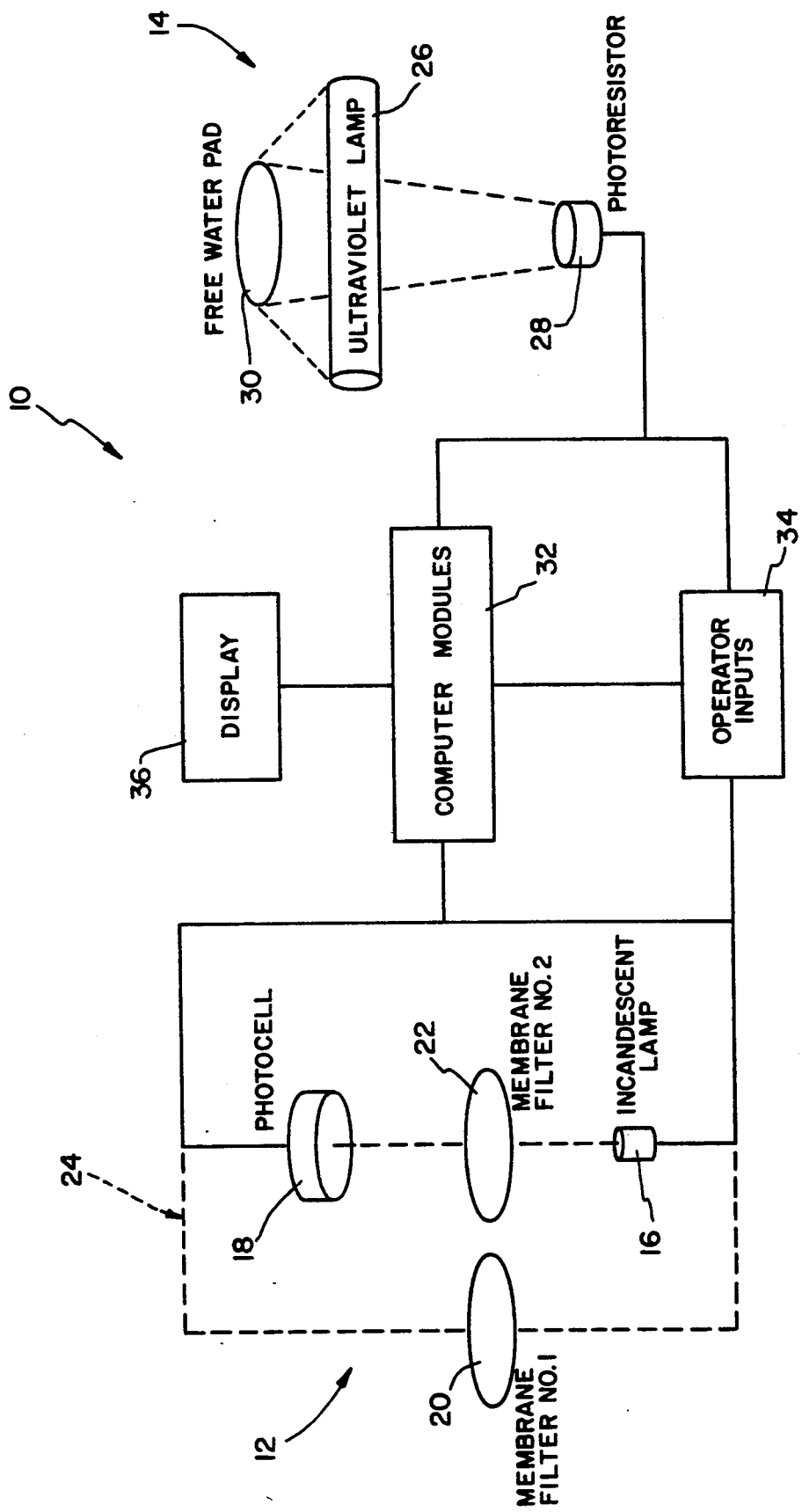
FIG. 1 is a diagrammatic representation of a fuel contamination detection system, in accordance with the principles of the present invention.

In an exemplary embodiment of the invention as shown in the drawings, and in particular by referring to the diagrammatic representation of FIG. 1, there is shown a fuel contamination detection system 10 including a particulate detector 12 and a free water detector 14. Particulate detector 12 includes an incandescent lamp 16 and a photocell 18, between which membrane filters 20 and 22 are selectively introduced by a filter slide assembly 24. Free water detector 14 includes an ultraviolet lamp 26 and a photoresistor 28, both arranged such that when a chemically treated water filter pad 30 is exposed to lamp 26 the photoresistor 28 responds to light fluorescing from pad 30. Both particulate detector 12 and free water detector 14 require computation circuitry 32, operator inputs 34, and a display 36 in order to conduct and indicate the results of their respective tests. In the preferred embodiment, photocell 18 is a Vactec VTS7070A photocell and photoresistor 28 is a Clairex CL5M5 photoresistor.

Generally, particulate detection is accomplished by sampling a known quantity of fuel through two standard membrane filters placed in series. The first filter acquires any particulate above its nominal porosity size. Additionally, the first filter acquires an amount of nonparticulate coloration proportionate to the quantity and quality of coloration present in the fuel sample. The second filter acquires little, if any, particulate contamination; however, it also acquires the fuel coloration. By processing and comparing the resulting opacities and coloration characteristics of the two sample filters, a resulting equivalent contamination weight for the fuel sample is determined and displayed in milligrams per liter (mg/L).

Likewise, free water detection is generally accomplished by using a water filter pad having a coating that chemically reacts with water, but not fuel, and changes color in response thereto. To negate individual pad differences, a freshly opened water filter pad is placed into the detection area prior to exposure to a fuel sample, and an initial value for that particular pad is established. A fresh fuel sample is then passed through the pad, whereupon the pad changes color in direct proportion to the quantity of undissolved water in the fuel sample. Detection is performed using ultraviolet light, as this greatly amplifies any resulting color change. The light intensity emitted by the exposed pad is compared to its initial value in order to determine and display the free water content of the fuel in parts per million (ppm).

Figure 2:
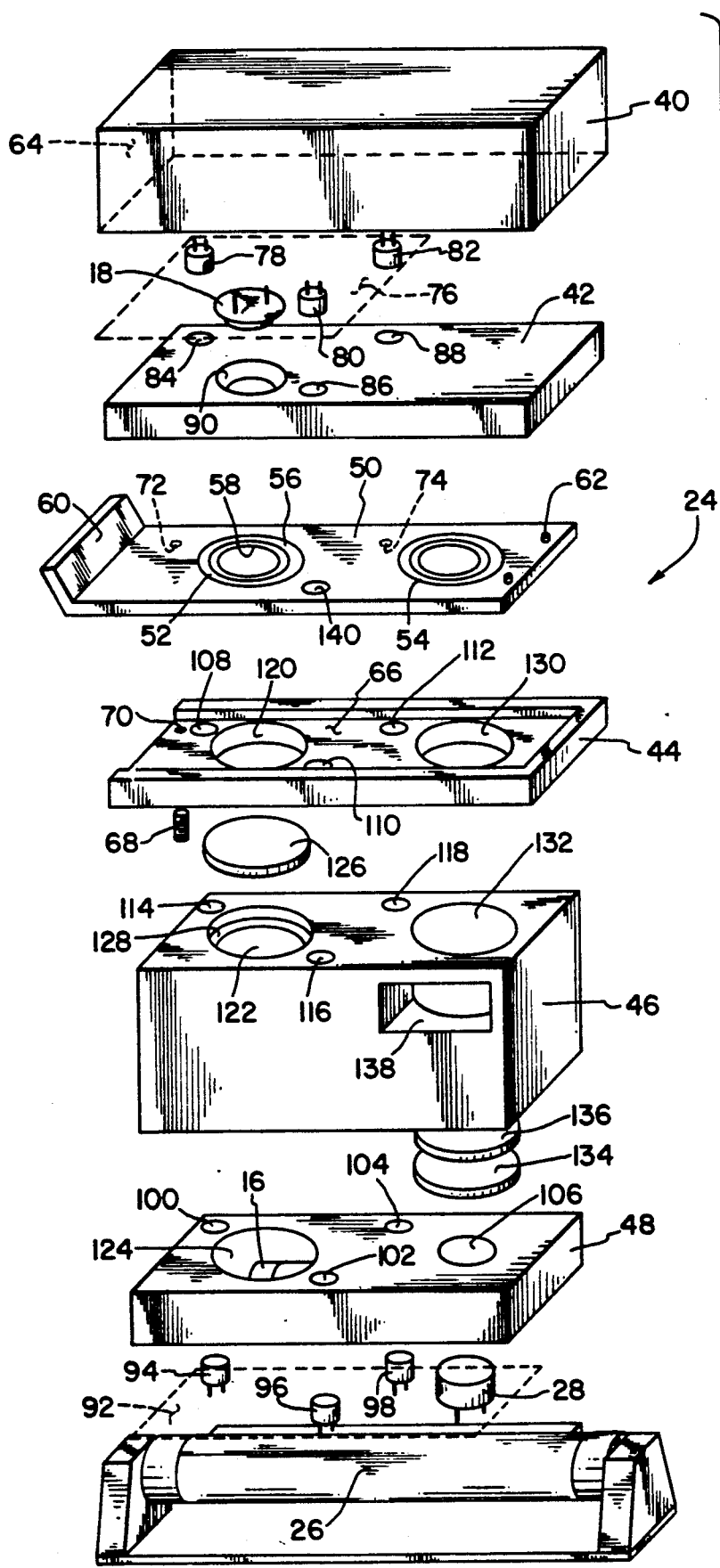
FIG. 2 is an exploded view of the filter handling assembly of the fuel contamination detection system of FIG. 1.

Filter slide assembly 24 will now be described with reference to FIG. 2. Assembly 24 includes a cover 40, a top sensor mounting plate 42, a slide base 44, a light block 46, and a bottom sensor mounting plate 48, wherein slide base 44 and light block 46 are mounted between top and bottom mounting plates 42 and 48 by a plurality of bolts (not shown). Cover 40 is frictionally retained, or otherwise engaged, with top mounting plate 42. A filter support slide 50 is slidably retained intermediate top mounting plate 42 and slide base 44, as will be more fully described hereinafter.

Filter support slide 50 includes a first aperture 52 and a second aperture 54 adapted to retain membrane filters 20 and 22, respectively. More specifically, slide 50 includes a stepped counterbore surrounding, or circumjacent, each of the first and second apertures 52 and 54, including a large diameter counterbore 56 on the surface of the slide and a small diameter 58 on the surface of counterbore 56. In this manner, two different sizes of membrane filters may be accommodated. For instance, membrane filters 20 and 22 of the preferred embodiment are Millipore membrane filters, as manufactured by Millipore Corporation of Bedford, Mass., measuring either 0.8 microns in nominal porosity and 37 millimeters in diameter for use in the commercial industry with pressure testing, or 0.45 microns in nominal porosity and 47 millimeters in diameter for use in laboratories with vacuum testing. When the sample filters are prepared by pressure sampling, best results are achieved by using the Accumetric monitor capsule with inlet dispersion, commercially available from Telectro-Mek, Inc. of Fort Wayne, Ind., and disclosed in U.S. Pat. No. 4,944,876.

Slide 50 further includes an upturned handle portion 60 that is grasped by an operator to selectively move the slide to various test positions. A pair of upwardly extending stop posts 62 provide interference with side 64 of cover 40, in order to limit the slide to a fully extended position out of slide base 44, without becoming disengaged therefrom Slide base 44 includes a three-sided slide channel 66 that, together with top mounting plate 42, provides the necessary space in which slide 50 moves An externally threaded, spring-biased detent ball assembly 68 is received within threaded hole 70. Detent ball assembly 68 cooperates with concave ball receptacles 72 and 74 formed in the bottom surface of slide 50, whereby the detent ball is yieldably received within a selected ball receptacle when the slide is in predetermined positions relative the slide base.

Filter slide assembly 24 includes means for sensing the position of slide 50 relative slide base 44, including optical switches that are opened and closed by movement of the slide. Specifically, a circuit board 76 on the top surface of top mounting plate 42 includes optical switch emitters 78, 80, and 82, which are received within holes 84, 86, and 88, respectively, in plate 42. Circuit board 76 also includes photocell 18 associated with particulate detector 12, which is received within a corresponding hole 90 in mounting plate 42.

A circuit board 92 on the bottom surface of bottom mounting plate 48 includes optical switch receivers 94, 96, and 98, which are received within holes 100, 102, and 104, respectively, in plate 48. Circuit board 92 also includes photoresistor 28 associated with free water detector 14, which is received within a corresponding hole 106. In the absence of filter support slide 50 within slide channel 66 of slide base 44, photo switch emitters 78, 80, and 82 have unobstructed communication with photo switch receivers 94, 96, and 98 through holes 108, 110, and 112 in slide base 44 and holes 114, 116, and 118 in light block 46, respectively. The manner in which the position of filter support slide 50 is determined by the optical switches will be described in further detailed hereinafter.

Filter slide assembly 24 permits the introduction of filter membranes 20 and 22 intermediate incandescent light 16 and photocell 18 during operation of particulate detector 12 by the provision of aligned holes therebetween; namely, hole 120 in slide base 44, hole 122 in light block 46, and hole 124 in bottom mounting plate 48. A frosted glass 126 is disposed within a counterbore 128 in light block 46 to diffuse light from light 16 before it is sensed by photocell 16. Slide assembly 24 also facilitates introduction of water filter pad 30, when retained within aperture 54, in proper registry with ultraviolet 26 and photoresistor 28 during operation of free water detector 14. Specifically, hole 130 in slide base 44 and hole 132 in light block 46 provide light communication between the water filter pad 30 and photoresistor 28. A plastic yellow filter 134, e.g., one third coefficient photographic filter, as well as a piece of clear glass 136, are disposed within a counterbore in the bottom surface of light block 46 to help filter out ultraviolet light and pass the yellow fluorescence of the water filter pad. Light block 46 includes a side access hole 138 in communication with hole 132, through which light from ultraviolet light 26 enters for exposure to the water filter pad.

It should be noted in connection with the foregoing description of filter slide assembly 24 that the interior surfaces of holes 130 and 132, i.e., the ultraviolet light chamber, are made black to enhance the reading of light fluorescing from the water filter pad, and the interior surfaces of holes 122 and 124, i.e., the particulate light chamber, are provided with a reflective coating to enhance the intensity of light emitted from incandescent light 16. The interior surface of side access hole 138 is also given a reflective coating to enhance introduction of the ultraviolet light into the ultraviolet light chamber.

Figure 3:
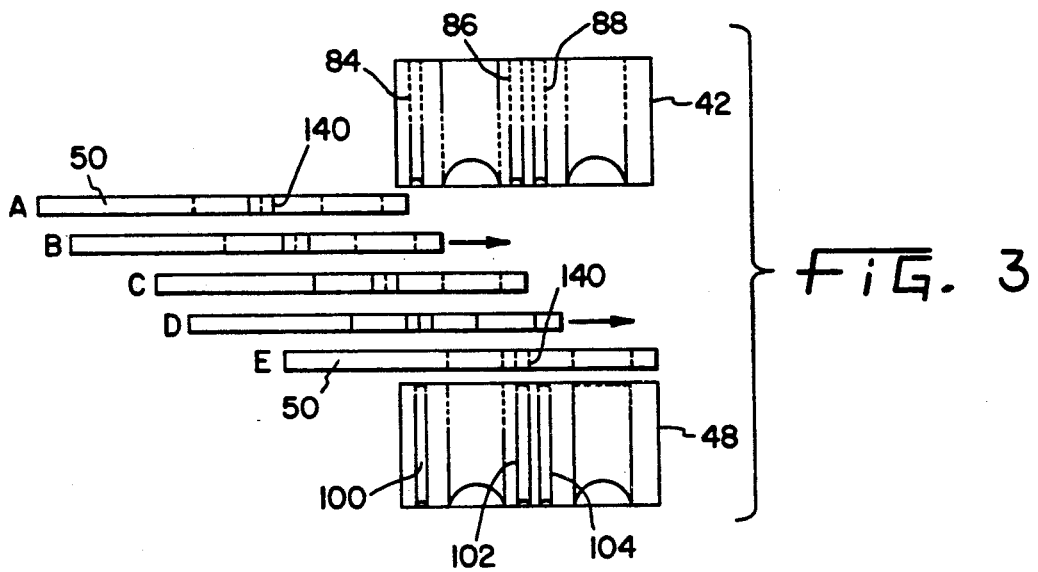
FIG. 3 shows the filter support slide of the filter handling assembly of FIG. 2 as it slides to various positions intermediate the upper and lower sensor mounting plates.
Figure 4:
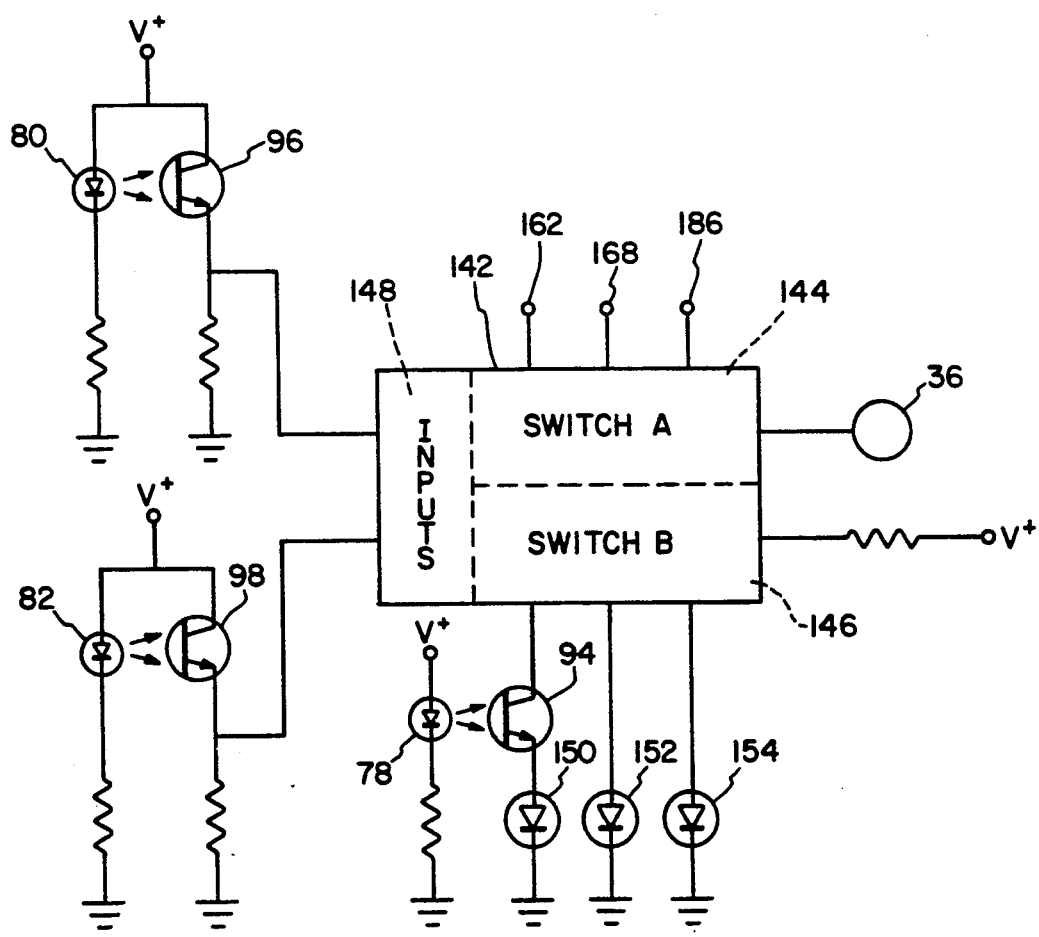
FIG. 4 is an electrical schematic diagram showing the optical switches and analog switch associated with sensing the position of the filter support slide of the filter handling assembly of FIG. 2.

Reference will now be made to FIGS. 3 and 4 concerning the manner in which the position of filter support slide 50 is determined by the aforementioned optical switches. As shown in FIG. 2, slide 50 includes a position determining hole 140 that is located so as to align with holes 86, 110, 116, and 102 when the slide is fully inserted into slide channel 66, i.e., apertures 52 and 54 are properly aligned for testing of the membrane filters. Movement of slide 50 so that hole 40 is out of alignment causes an interruption in the light path between emitter 80 and receiver 96. The light path is reestablished when slide 50 is retracted sufficiently to no longer obstruct the path. Similarly, the light path between emitter 78 and receiver 94 and between emitter 82 and receiver 98 are interrupted by slide 50 as it is moved in and out of selected positions.

Referring to FIG. 4, a multiplex switch 142 provides separate switching of a Switch A designated at 144 and a Switch B designate at 146, based upon a pair of control inputs designated at 148. One example of such a double pole analog switch is the Motorola MC14052BCP multiplex switch. As shown in FIG. 4, the outputs of photo switch receivers 96 and 98 provide logical high or low inputs to switch 142, which then multiplexes four possible inputs to a single output (Switch A 144), or one input to four possible outputs (Switch B 146), only three of which are being used here in each case. Switch B 146 is configured to illuminate light emitting diodes (LED's) 150, 152, or 154 from a voltage supply input, based upon the conditions of emitters 96 and 98. Additionally, the output to LED 150 is dependent upon the condition of receiver 94.

In FIG. 3, filter support slide 50 is shown in positions A through E, progressively moving from a fully extended or loading position A, to a first test position C, and then to a second test position E. Positions B and D represent movement of the slide between adjacent positions. In position A, each of photo switch receivers 94, 96, and 98 will have unobstructed light and, therefore, will be energized, whereby Switch B 146 will permit the illumination of LED 150 During movement of the slide through position B, receiver 94 is no longer energized, thereby turning off LED 150. At first test position C, the light to receiver 96 becomes obstructed by the slide, whereby that input to switch 142 goes low causing LED 152 to be energized by Switch B according to predetermined logical switching. During movement of the slide through position D, the light to receiver 98 becomes obstructed as well, whereby both inputs to switch 142 go low causing LED 152 to turn off. Lastly, at second test position E, position sensing hole 140 of slide 50 is aligned such that receiver 96 is energized while emitters 94 and 98 remain deenergized, whereby this combination of control inputs causes LED 154 to turn on. Accordingly, only one LED is illuminated at a time; namely, LED 150 is turned on at position A, LED 152 is turned on at position C, and LED 154 is turned on at position E. During movement of the slide through positions B and D, none of the LED's is turned on, thereby avoiding the potential for operator confusion.

Switch A 144 of multiplex switch 142 functions during operation of particulate detector 12 to switch display 36, e.g., a digital meter, between various input signals from the computation circuitry of the particulate detector, as will be more fully described hereinafter as the computation circuitry is described.

Fuel contamination detection system 10 is selectively operable as particulate detector 12 or as free water detector 14, by virtue of a function switch that energizes the respective circuitry associated with each detector In the preferred embodiment of the present invention, the aforementioned multiplex switch 142 is operable only during the particulate detector mode of the system for indicating test sequencing by the lighting of LED's 150, 152, and 154, as will be more fully described. Upon selection of the free water detector mode, these LED's are no longer energized in response to movement of the filter support slide. Instead, a single LED responsive to the function switch may be illuminated to indicate that the system is in the free water detection mode.

Figure 5:
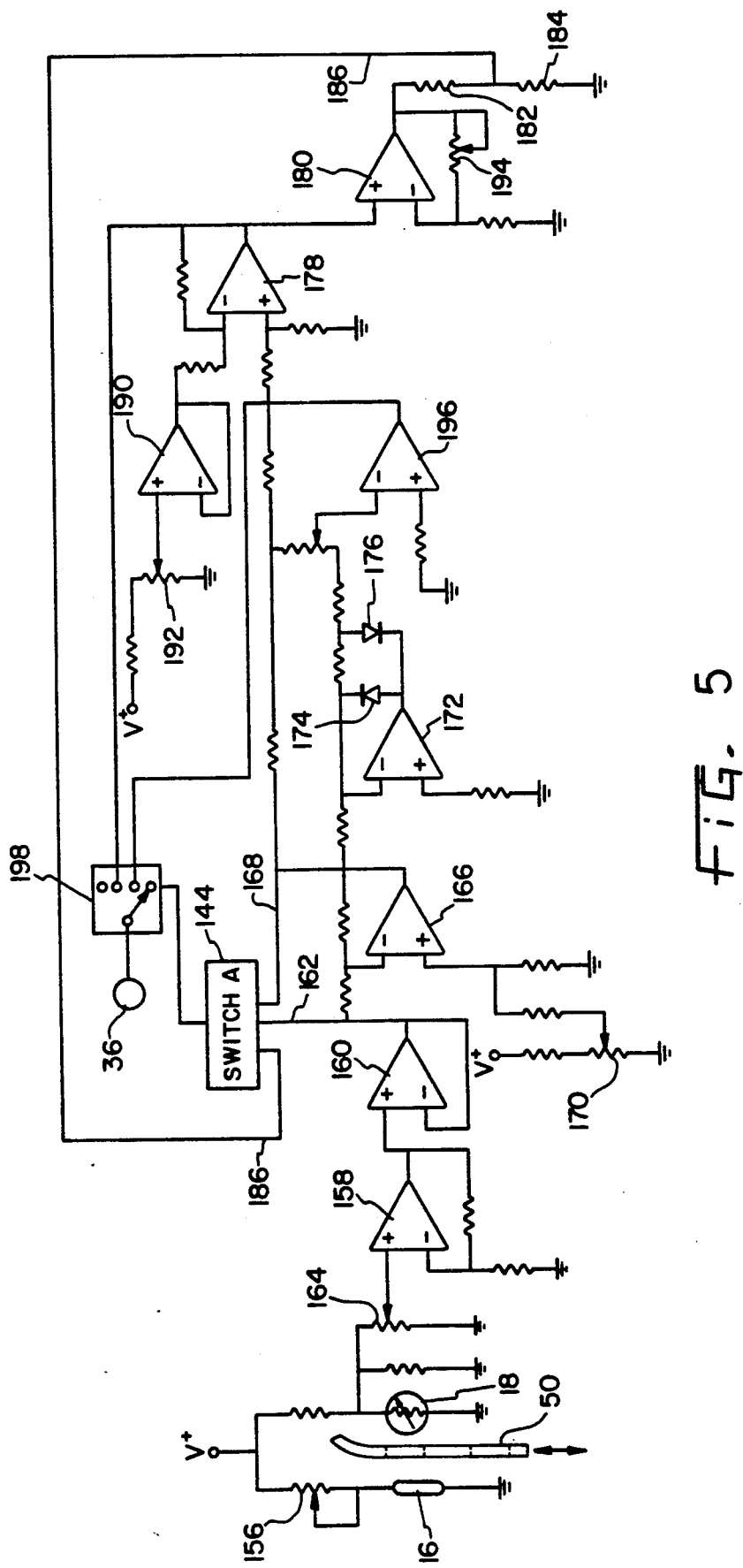
FIG. 5 is a circuit diagram of the particulate detector circuit of the fuel contamination detection system of FIG. 1.

Referring to FIG. 5, the computation circuitry associated with particulate detector 12 will now be described. Incandescent light 16 is shown connected to positive voltage source V+ through a variable resister 156 which allows the intensity of the light to be varied, if desired. With slide 50 initially in position A of FIG. 3, photocell 18 is exposed directly to light from light 16. The voltage signal across photocell 18 is applied to the noninverting input of an operation amplifier 158 which amplifies the signal. The output of amplifier 158 is buffered through an operation amplifier 160, the output of which constitutes an input 162 to Switch A 144 of multiplex switch 142. With slide 50 in position A, Switch A 144 is configured to connect input 162 to display 36 at the same time that Switch B 146 is energizing LED 150. The illumination of LED 150 prompts the operator to manually adjust a variable resister 164 so that the reading on display 36 is a predetermined value representing a standard maximum output.

The output of amplifier 160 is also connected to the inverting input of an operational amplifier 166, the output of which constitutes an input 168 to Switch A 144. When slide 50 is in position C, Switch A 144 is configured to connect input 168 to display 36 at the same time that Switch B 146 is energizing LED 152. Position C of slide 50 corresponds to a first test position whereat membrane filter 22 is intermediate light 16 and photocell 18. The illumination of LED 152 prompts the operator to manually adjust a variable resistor 170 that is coupled to the noninverting input of amplifier 166 in a manner to adjust the voltage level of the input. Amplifier 166 is configured as a differential amplifier and, therefore, changing the noninverting input by adjustment of resistor 170 allows the operator to adjust the output of amplifier 166 to produce a zero reference signal. In the preferred embodiment, illumination of LED 152 prompts the operator to adjust resistor 166 until a zero reference readout is achieved on display 36. More importantly, the setting of resistor 170 provides a memory function and a basis from which a differential reading of filter opacities can be determined.

The output of amplifier 166 is connected to an absolute value network including operational amplifier 172 and diodes 174 and 176. The output of the absolute value network is coupled through a differential operational amplifier 178 and a scaling operational amplifier 180, the output of which is connected to a resistive voltage divider network including resistors 182 and 184. The output of the voltage divider constitutes an input 186 to Switch A 144.

When slide 50 is moved to position E, Switch A 144 is configured to connect input 186 to display 36 at the same time that Switch B 146 is energizing LED 154. The illumination of LED 154 prompts the operator to read from display 36 the differential opacity reading of the test filters representing particulate contamination in mg/L. The circuitry of the particulate detector may optionally include offset calibration means comprising an operation amplifier 190, the output of which is connected to the inverting input of amplifier 178. A variable resistor 192 permits a variable voltage signal to be applied to amplifier 190 and, thus, to amplifier 178, in order to calibrate the test for use with different fuels. However, resistor 192 is set so that the output of amplifier 190 is zero during use of the test with standard turbine engine fuels, such as Jet A, Jet Al, JP-4, JP-5, etc. A variable resistor 194 associated with amplifier 180 also provides calibration for varying the relationship of opacity measurements to display outputs Operational amplifier 196 allows a calibration technician to monitor a test signal on the display monitor A switch 198 ordinarily connects Switch A to display 36; however, during calibration a technician can optionally monitor the outputs of operation amplifiers 178 and 196 on display 36.

Figure 6:
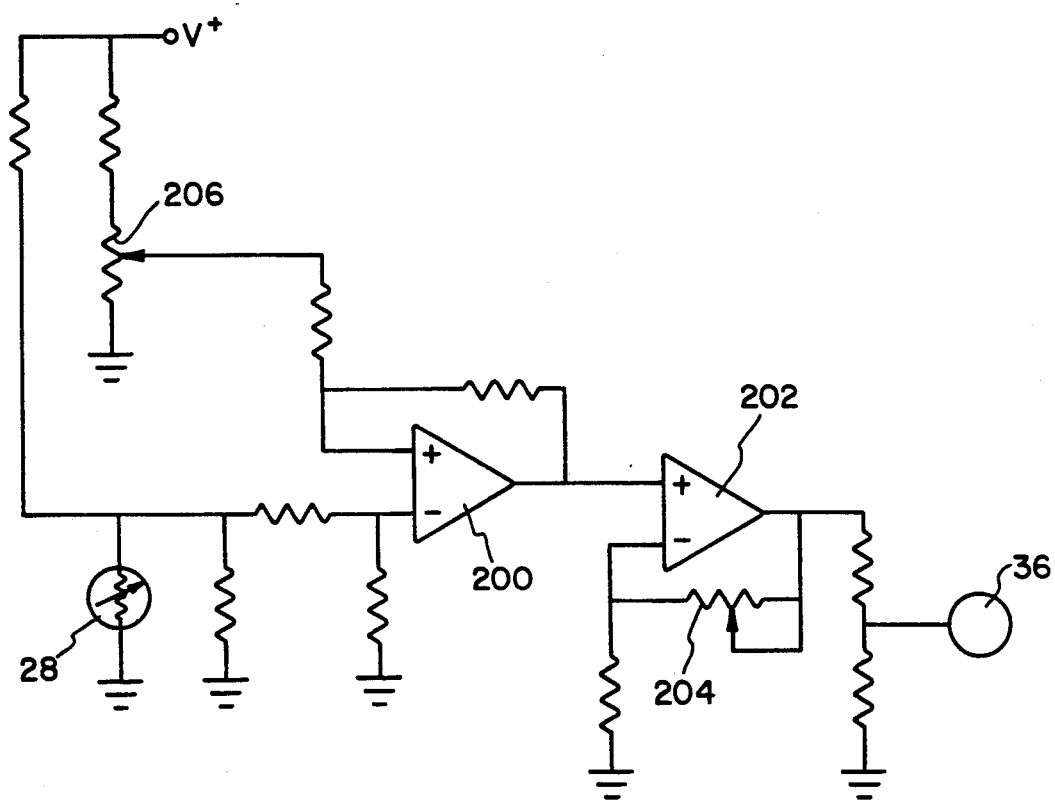
FIG. 6 is a circuit diagram of the free water detector circuit of the fuel contamination detection system of FIG. 1.

Referring to FIG. 6, the free water detector circuitry is disclosed. Essentially, an operational amplifier 200 is configured as a differential amplifier to compare the output of photoresistor 28 with a manually adjustable reference signal. Specifically, a voltage signal dependent upon the output of photoresistor 28, i.e., the intensity of light fluorescing from a sample water filter pad, is connected to the inverting input of amplifier 200. The output of amplifier 200 is connected to the noninverting input of an operation amplifier 202 which as a scaling amplifier adjustable by a variable resistor 204. The output of amplifier 202 is connected through a voltage divider network to display 36. In the preferred method of conducting the free water detector, an unwetted water filter pad is first placed adjacent ultraviolet light and photoresistor 28, at which time a variable resistor is manually adjusted by the operator in order to vary the voltage input to the noninverting input of amplifier 200 to achieve a zero reading on display 36. Once the display register zero, a fuel sample is passed through that same water filter pad and then retested. The output of photoresistor 28 will change in relationship to the intensity of light fluorescing from the water filter pad, whereby a measure of the free water contamination with be displayed. Accordingly, variable resistor 206 provides a memory function and establishes a basis from which a differential reading of the acquired free water contamination of a water filter pad can be determined.

In the preferred embodiment of the fuel contamination detection system of the present invention, the fuel sample size must be varied according to the membrane filter size in order to produce consistent results independent of the size of the filter membrane. For instance, for the particulate detector a 700 ml fuel sample is used for a 37 mm membrane filter and a 800 ml fuel sample size is used for a 47 mm membrane filter. For the free water detector a 450 ml fuel sample size is used for the 37 mm water filter pad, while a 500 ml fuel sample size is used for the 47 mm water filter pad.

In the preferred embodiment of the invention, the chemical coating on the water filter pad has the ability to absorb free water from the fuel passed therethrough, and may consist of a potassium or sodium salt composition. In either case, the material has the property of fluorescing in proportion to the amount of free water collected by the salt during the passage of the fuel sample through the water filter pad.

The power supply for the devices and circuitry of the disclosed embodiment of the fuel contamination detection system is conventional and should include the necessary regulated voltages to power the light sources and electronic components. In the preferred embodiment, wherein the system is housed in a portable carrying case, a rechargeable battery power supply includes a low battery alarm and a recharging circuit connectable to a source of alternating current. The system may alternatively be powered by the A.C. power source.

It will be appreciated that the foregoing description of a preferred embodiment of the invention is presented by way of illustration only and not by way of any limitation, and that various alternatives and modifications may be made to the illustrated embodiment without departing from the spirit and scope of the invention.

What is claimed is:

1. In a fluid contamination detection system configured and arranged such that a fluid sample containing particulates is passed successively through a first filter element that both traps the particulates and acquires the coloration of the fluid sample and a second filter element that only acquires the coloration of the fluid sample, a particulate detection apparatus, comprising:
   a light source;
   photosensing means responsive to light from said light source for providing an indication of light intensity;
   a filter support slide including a first aperture and a second aperture, said slide being movable between a first position whereat said first aperture is intermediate said light source and said photosensing means and a second position whereat said second aperture is intermediate said light source and said photosensing means, said slide being adapted to support the first filter element over said first aperture and the second filter element over said second aperture, thereby causing the first and second filter elements to be intermediate said light source and said photosensing means when said slide is in said first and second positions, respectively;
   opacity measuring means responsive to said photosensing means for measuring the respective opacities of the first and second filter elements when said slide is in said first and second positions, respectively; and
   indicating means for providing an indication dependent upon said measured opacities of the first and second filter elements, whereby detection of particulate levels in the fluid sample is performed without further handling of said first and second filter elements once they are placed in supporting relationship on said filter support slide, thereby minimizing filter contamination and resulting measurement error.

2. The fluid contamination detection system of claim 1, and further comprising:
   a slide base, intermediate said light source and said photosensing means, in which said filter support slide is slidably disposed, said slide base including a first opening corresponding to said first aperture through which light emanating from said light source is exposed to said photosensing means.

3. The fluid contamination detection system of claim 2 in which:
   said slide base includes a slide channel in which said filter support slide moves between said first position wherein said slide occupies substantially the entire said channel, said second position wherein said slide occupies approximately half of said channel, and a fully extended position wherein said slide is substantially removed from said channel and is spaced from a position intermediate said light source and said photosensing means to thereby unobstructedly exposed said photosensing means to light emanating from said light source 4. The fluid contamination detection system of claim 3, and further comprising:
   cover means connected to said slide base for covering said slide channel, said filter support slide including stop means engaging said cover means when said slide is in said fully extended position for preventing sliding movement of said slide beyond said fully extended position and out of sliding engagement with said slide base.

5. The fluid contamination detection system of claim 2, and further comprising:
   detent means cooperating between said filter support slide and said slide base for yieldably retaining said slide in a predetermined position relative said slide base.

6. The fluid contamination detection system of claim 5 in which:

said predetermined position of said filter support slide relative said slide base is with said one of said first and second apertures intermediate said light source and said photosensing means.

7. The fluid contamination detection system of claim 5 in which:
said detent means includes a spring-biased detent ball connected to said slide base, and a ball receptacle on said filter support slide, whereby said detent ball is yieldably received within said ball receptacle when said slide is at said predetermined position relative said slide base.

8. The fluid contamination detection system of claim 1 in which:
said filter support slide comprises a generally flat plate having a top surface on which said first and second apertures open, said plate including respective first counterbores in said top surface circumjacent said first and second apertures which are adapted to retain a first size of filter elements, said plate further including respective second counterbores within said first counterbores which are adapted to retain a second size of filter elements smaller than said first size.

9. The fluid contamination detection system of claim 1, and further comprising:
light diffusing means adjacent said photosensing means for diffusing light emanating from said light source before exposure thereof to said photosensing means.

10. In a fluid contamination detection system configured and arranged such that fluid sample containing particulates is passed successively through a first filter element that both traps the particulates and acquires the coloration of the fluid sample and a second filter element that only acquires the coloration of the fluid sample, a particulate detection apparatus, comprising:
a light source;
photosensor means for providing a light intensity signal indicative of the intensity of light from said light source;
a filter support slide including a first aperture and a second aperture, said slide being movable between a first position whereat said first aperture is intermediate said light source and said photosensor means and a second position whereat said second aperture is intermediate said light source and said photosensor means, said slide being adapted to support the first filter element over said first aperture and the second filter element over said second aperture, thereby causing the first and second filter elements to be intermediate said light source and said photosensor means when said slide is in said first and second positions, respectively;
position sensing means for providing a position signal indicative of said positions of said slide in one of said first and second positions;
circuit means responsive to said light intensity signal and said position signal for providing a reference signal when said slide is in one of said first and second positions and a comparative signal when said slide is in the other of said first and second positions, each of said reference signal and said comparative signal being indicative of filter element opacity associated with the corresponding position of said slide; and
display means responsive to said circuit means for providing a contamination level indication dependent upon said reference signal and said comparative signal and representing of particulates in the fluid sample.

11. The fluid contamination detection system of claim 10 in which:
said position sensing means includes an optical switch, and said filter support slide includes a hole therein with which said optical switch operably cooperates when said slide is in said one of said first and second positions to provide said position signal.

12. The fluid contamination detection system of claim 10 wherein said position sensing means provides a second position signal indicative of said filter support slide being in said second position, and said circuit means provides said reference signal when said slide is in said second position, and further comprising:
a second position indicating light that is illuminated in response to the presence of said second position signal, said circuit means including manually adjustable means for offsetting both said reference signal and said comparative signal such that said display means registers approximately zero in response to said reference signal, whereby indication of said comparative signal by said display means represents a measure of a particulate level in the fluid sample independent of fluid coloration.

13. The fluid contamination detection system of claim 12 wherein said position sensing means further provides a first position signal indicative of said filter support slide being in said first position, and further comprising:
a first position indicating light that is illuminated in response to said first position signal, whereby said first indicating light informs an operator that said display means is providing a measure of the particulate level in the fluid sample.

14. The fluid contamination detection system of claim 10, and further comprising:
light diffusing means adjacent said photosensing means for diffusing light emanating from said light source before exposure thereof to said photosensing means.

15. A fuel contamination detection system selectively operable in a first mode as a particulate detector and operable in a second mode as a free water detector configured and arranged such that for the particulate detector a first fuel sample containing particulates is passed successively through a first filter element that both traps the particulates and acquires the coloration of the fluid sample and a second filter element that only acquires the coloration of the fluid sample, and for the free water detector a second fuel sample is passed through a water filter pad treated with chemicals that when exposed to ultraviolet light fluoresce at an intensity dependent upon the amount of free water in the fuel sample, comprising:
an incandescent light source;
first photosensing means responsive to said incandescent light source for providing an indication of light intensity emanating therefrom;
a filter support slide including a first aperture and a second aperture, said slide being movable between a first position whereat said first aperture is intermediate said incandescent light source and said first photosensing means and a second position whereat said second aperture is intermediate said light source and said first photosensing means, said slide being adapted in said first mode to support the first filter element over said first aperture and the second filter element over said second aperture, thereby causing the first and second filter elements to be intermediate said incandescent light source and said first photosensing means when said slide is in said first and second positions, respectively;

an ultraviolet light source, said second aperture of said slide being adjacent said ultraviolet light source when said slide is in said second position, said slide being adapted in said second mode to support the water filter pad over said second aperture, thereby causing the water filter pad to be adjacent said ultraviolet light source and exposed to ultraviolet light therefrom when said slide is in said second position;

second photosensing means for providing an indication of intensity of light fluorescing from the water filter pad in response to exposure to ultraviolet light from said ultraviolet light source;

circuit means responsive to said first photosensing means for measuring the respective opacities of the first and second filter elements when the fuel contamination detection system is operable in its first mode as a particulate detector, and responsive to said second photosensing means for measuring the intensity of light fluorescing from the water filter pad when the fuel contamination detection system is operable in its second mode as a free water detector; and display means responsive to said circuit means for providing in the first mode of the system a first contamination level indication dependent upon the measured opacities of the first and second filter elements and representing particulates in the first fluid sample, and providing in the second mode of the system a second contamination level indication dependent upon measured intensity of light fluorescing from the water filter pad and representing free water in the second fluid sample.

16. The fuel contamination detection system of claim 15 in which:

said circuit means provides a free water signal indicative of said measured intensity of light fluorescing from the water filter pad, said circuit means including manually adjustable means for offsetting said free water signal such that said display means can be made to register approximately zero in response to a free water signal generated by testing the water filter pad before the second fuel sample is passed therethrough, whereby said second contamination level indication provided by said display means represents a measure of free water level independent of variations in the initial fluorescence of the water filter pad.

17. The fuel contamination detection system of claim 15, and further comprising:

light filtering means, intermediate said ultraviolet light source and said second aperture when said filter support slide is in said second position, for blocking ultraviolet light and passing yellow fluorescent light from the water filter pad.

18. The fuel contamination detection system of claim 15, and further comprising:

light diffusing means adjacent said first photosensing means for diffusing light emanating from said incandescent light source before exposure thereof to said first photosensing means.

* * * * *

UNITED STATES PATENT AND TRADEMARK OFFICE
CERTIFICATE OF CORRECTION

PATENT NO. : 5,200,064
DATED : April 6, 1993
INVENTOR(S) : Daniel G. Russ et al.

It is certified that error appears in the above-identified patent and that said Letters Patent is hereby corrected as shown below:

Col. 1, lines 36-37, change "coIoration" to --coloration--;

Col. 7, line 15, insert "." after "150".

Col. 7, line 46, insert "." after "tector".

Signed and Sealed this

Seventh Day of December, 1993

Attest:

BRUCE LEHMAN

Attesting Officer

Commissioner of Patents and Trademarks